United States Patent [19]
Ramanujam et al.

[11] Patent Number: 5,599,660
[45] Date of Patent: Feb. 4, 1997

[54] METHOD AND PREPARATION FOR SEQUENTIAL DELIVERY OF WAX-EMBEDDED, INACTIVATED BIOLOGICAL AND CHEMICAL REAGENTS

[75] Inventors: Rama P. Ramanujam; Brent A. Burdick, both of Brookfield, Wis.; Ulf D. Landegren; Pierre Sevigny, both of Upsala, Sweden

[73] Assignee: Pharmacia Biotech Inc., Milwaukee, Wis.

[21] Appl. No.: 349,115

[22] Filed: Dec. 2, 1994

Related U.S. Application Data

[63] Continuation-in-part of Ser. No. 227,835, Apr. 14, 1994, abandoned, which is a continuation-in-part of Ser. No. 4,883, Jan. 19, 1993, abandoned.

[51] Int. Cl.$^6$ .............................. C12Q 1/68; C12P 19/34; C10G 73/36
[52] U.S. Cl. .................... 435/4; 435/6; 435/91.2; 436/8; 436/94; 208/20; 208/21
[58] Field of Search .................... 435/4, 6, 91.2, 435/91.1; 436/8, 94; 208/20, 21

[56] References Cited

U.S. PATENT DOCUMENTS

| | | | |
|---|---|---|---|
| 3,897,308 | 7/1975 | Li et al. | 195/63 |
| 4,935,339 | 6/1990 | Zahradnik | 435/5 |
| 4,940,665 | 7/1990 | Iijima et al. | 435/187 |
| 5,017,256 | 5/1991 | Ohtomo et al. | 156/240 |
| 5,098,893 | 3/1992 | Franks et al. | 514/54 |
| 5,310,885 | 5/1994 | Maier et al. | 530/413 |
| 5,411,876 | 5/1995 | Bloch et al. | 435/91.2 |
| 5,413,924 | 5/1995 | Kosak et al. | 435/177 |

FOREIGN PATENT DOCUMENTS

| | | |
|---|---|---|
| 0448930A1 | 2/1991 | European Pat. Off. |
| 0545547A2 | 2/1992 | European Pat. Off. |
| 0572057A1 | 1/1993 | European Pat. Off. |
| 9112342 | 8/1991 | WIPO. |
| WO92/17769 | 10/1992 | WIPO. |

OTHER PUBLICATIONS

Okahata et al., *J. Am. Chem. Soc.* 114, 8299–8300 (1992).
Ramanujam et al., *Bio Techniques* 14(3), 470–474 (1993).
Bassam, et al., "Automated 'Hot Start' PCR Using Mineral Oil and Paraffin Wax," *Biotechniques* 14:31–33, 1993.
Chou, et al., "Prevention of pre–PCR mis–priming and primer dimerization improves low–copy–number amplifications," *Nucl. Acids Res.* 20:1717–1723, 1992.
D'Aquila, et al., "Maximizing sensitivity and specificity of PCR by preamplification heating," *Nucl. Acids Res.* 19:3749, 1991.
Darnell, et al., *Molecular Cell Biology*, pp. 63–66, 1986, published: Scientific American Books, NY, NY.
Earley, et al., "Efficient DNA sequencing on microtiter plates using dried reagents and Bst DNA polymerase," *DNA Sequence—J. DNA Sequencing and Mapping* 4:79–85, 1993.
Erlich, et al., "Recent Advances in the Polymerase Chain Reaction," *Science* 252:1643–1651, 1991.
Goelz, et al., "Purification of DNA From Formaldehyde Fixed and Paraffin Embedded Human Tissue," *Biochem. and Biophys. Res. Commun.* 130[1]:118–126, 1985.
Heller, et al., "An Efficient Method for the Extraction of DNA from Formalin–Fixed, Paraffin–Embedded Tissue by Sonication," *Biotechniques* 11[3]:372–377, 1991.

(List continued on next page.)

*Primary Examiner*—Kenneth R. Horlick
*Attorney, Agent, or Firm*—Quarles & Brady

[57] ABSTRACT

A method and preparation for the storage and delivery of purified reagents is disclosed. In one aspect, the preparation comprises an amount of a first wax carrier, the first wax carrier having a first melting point, and an amount of a first reagent, wherein first reagent is a substantially purified preparation of at least one biological or chemical reagent. The first wax carrier and the first reagent are combined to form a solid first reagent portion. The solid mixture is combined with a second reagent portion comprised of at least one biological or chemical reagent in an inactive form.

26 Claims, 1 Drawing Sheet

OTHER PUBLICATIONS

Impraim, et al., "Analysis of DNA Extracted from Formalin–Fixed, Paraffin–Embedded Tissues by Enzymatic Amplification and Hybridization with Sequence–Specific Oligonucleotides," *Biochem. and Biophys. Res. Commun.* 142[3]:710–716, 1987.

Kaijalainen, et al., "An alternative hot start technique for PCR in small volumes using beads of wax–embedded reaction components dried in trehalose," *Nucl. Acids Res.* 21:2959–2960, 1993.

Katzman, "Use of Oil Overlays in 'Oil–Free' PCR Technology," *Biotechniques* 4:36–40, 1993.

Kwok, et al., "Avoiding false positives with PCR," *Nature* 339:237–238, 1989.

Lagerström, et al.; "Capture PCR: Efficient Amplification of DNA Fragments Adjacent to a Known Sequence in Human and YAC DNA," *PCR Meth. and Applic.* 1:111–119, 1991.

Lai–Goldman, et al., "Detection of Human Immunodeficiency Virus (HIV) Infection in Formalin–Fixed, Paraffin–Embedded Tissues by DNA Amplication," *Nucl. Acids Res.* 16[16]:8191, 1988.

Limitekk Advertisement, *Biotechniques* Apr. 1994.

Mullis, "The Polymerase Chain Reaction in an Anemic Mode: How to Avoid Cold Oligodeoxyribonuclear Fusion," *PCR Methods and Applications* 1:1–4, 1991.

Parik, et al., "A Manifold Support for Molecular Gentic Reactions," *Anal. Biochem.* 211:144–150, 1993.

Perkin–Elmer Corporation – Pamphlet on AmpliWax PCR Gems – Mar. 1992.

Rey, "Glimpses into the Fundamental Aspects of Freeze–drying," *Devel. Biol. Stand.* 36:19–27, 1977.

Ruano, et al., "Heat–Soaked PCR: An Efficient Method for DNA Amplification with Applications to Forensic Analysis," *Biotechniques* 13:266–274, 1992.

Saiki, et al., "Primer–Directed Enzymatic Amplification of DNA with a Thermostable DNA Polymerase," *Science* 239:487–491, 1988.

Shi, et al., "Direct Reverse Transcription—Polymerase Chain Reaction from Whole Blood Without RNA Extraction," *GATA* 9(5–6):149–150, 1992.

Smith, et al., "Extraction of Cellular DNA from Human Cells and Tissues Fixed in Ethanol," *Anal. Biochem.* 160:135–138, 1987.

Stanta, et al., "RNA Extracted from Paraffin–Embedded Human Tissues is Amenable to Analysis by PCR Amplification," *Biotechniques* 11[3]:304–308, 1991.

Takezawa, et al., "Cell Culture on a Thermo–responsive Polymer Surface," *Bio/Technol.* 8:854–856, 1990.

Veres, et al., "The Molecular Basis of the Sparse Fur Mouse Mutation," *Science* 237:415–417, 1987.

Wainwright, et al., "Parafin Beads Can Replace Mineral Oil as an Evaporation Barrier in PCR," *Biotechniques* 14:35–36, 1993.

Watson, et al., "Molecular Biology of the Gene," pp. 734–735, 1976.

METHOD AND PREPARATION FOR SEQUENTIAL DELIVERY OF WAX-EMBEDDED, INACTIVATED BIOLOGICAL AND CHEMICAL REAGENTS

RELATED APPLICATIONS

This application is a continuation-in-part of U.S. Ser. No. 08/227,835 filed Apr. 14, 1994, abandoned, which is a continuation-in-part of U.S. Ser. No. 08/004,883 which was filed Jan. 19, 1993, abandoned.

FIELD OF THE INVENTION

In general, the field of the present invention is the stabilization and delivery of purified reagents for chemical and biochemical reactions. Specifically, the field of the present invention is the stabilization and sequential delivery of reagents such as buffered enzymes and nucleic acid polymers by combining the reagents with a carrier wax.

BACKGROUND OF THE INVENTION

It is frequently necessary to combine reagents in a biochemical or chemical reaction. Typically, biological reagents such as proteins and nucleic acid polymers are delivered from aqueous solutions or suspensions or from freeze-dried material.

There are many problems associated with using aqueous solutions for reagent delivery. Proteins in an aqueous solution or suspension may be subject to rapid decomposition and loss of activity. Therefore, aqueous solutions or suspensions must usually be stored at a low temperature. Additionally, it is difficult to combine an aqueous reagent solution with a general reaction mixture without the reagents reacting immediately. Pipetting and dispensing aqueous reagents can be subject to measurement errors. It is also difficult to automate the delivery of aqueous reagents. There is always a potential for cross-contamination when aqueous reagents are repetitively pipetted from mixture to mixture.

Another method for storage and delivery of biological reagents involves drying the reagent. However, freeze-drying and other drying methods must rely on special drying and storage processes to stabilize and deliver reagents for molecular manipulations. For example, WO 87/00196 describes a method for the preservation of biological samples by drying in the presence of trehalose. U.S. Pat. No. 5,098,893 describes storage of material in a glassy or rubbery composition consisting of water-soluble or water-swellable carbohydrates and derivatives. EPA 0298669 describes an apparatus and method for performing nucleic acid manipulations utilizing predetermined amounts of reagents in a dry state. WO 84/03715 and WO 84/03444 describe a method in which reagents and antibodies may be provided in lyophilized form. Expensive and cumbersome methods and equipment, such as vacuum ovens, are required to preserve and deliver dried reagents.

What is needed in the art of molecular biology is an improved method of storing and sequentially delivering reagents in a biochemical or chemical reaction mixture. The present invention relates to a method of storing and sequentially delivering reagents by combining at least one of the reagents with a wax carrier material.

Clinical tissue samples have been stored in paraffin to preserve biologically inactive material for clinical sectioning and subsequent microscopic visualization. DNA has been extracted for PCR amplification from tissue samples prepared for routine histopathological examinations (Goelz, et al., *Biochem. Biophys. Res. Commun.* 130:118–126, 1985). RNA has been extracted and PCR-amplified from paraffin-embedded human tissue samples (Stanta and Schneider, *BioTechniques.* 11:304–308, 1991).

Wax has been used as an addition to enzymatic reactions. For example, a recent refinement in the polymerase chain reaction (PCR) process has been the use of AMPLIWAX (Perkin Elmer Cetus) and the development of the "Hot Start" technique. These refinements involve the replacement of mineral oil with a wax pellet as a vapor barrier and to increase amplification specificity (Chou, al., *Nucl. Acids Res.* 20 [7] 1717–1723, 1992). WO 91/12342 discloses the use of waxes and greases as vapor barriers in PCR reactions. Additionally, WO 91/12342 discloses subsets of PCR reagents, such as $Mg^{+2}$, as aqueous emulsions in a grease or wax barrier. European Patent Application 0572057 discloses PCR reagents in inert, meltable materials.

SUMMARY OF THE INVENTION

The present invention is a reagent preparation comprising a first wax carrier and a substantially purified preparation of at least one biological or chemical reagent, wherein the first wax carrier and the first reagent form a solid first reagent portion. The first wax carrier has a first melting point. The reagent preparation also comprises a substantially purified preparation of at least one biological or chemical reagent in an inactive form in a second reagent portion. The reagent preparation allows the second reagent portion to be released into a reaction medium while allowing the first reagent portion to be stabilized in an inactive form in a solid wax carrier portion. At an approximate time in the reaction, the first reagent can be released from the wax carrier.

In a preferred form, the second reagent is coated onto the surface of the first reagent.

In another embodiment of the present invention, the reagent preparation additionally comprises a third reagent portion available to be released at a different time than the first and second reagent portions.

In another embodiment of the present invention, the first or second reagent mixture comprises a plurality of reagents.

Preferably, the first melting point is greater than approximately 37° C.

Also preferably, the second reagent portion is stored in either a glassified form, a dehydrated form, or a second wax with second melting point.

Preferably, the first and second reagent portions comprise reagents selected from the group consisting of enzymes, structural proteins, nucleic acids, DNA, RNA, oligonucleotide probes, and buffer solutions.

The present invention is also a method of sequentially delivering reagents in a chemical or biological reaction. First, one obtains the reagent preparation of claim 1 and places it in contact with a reaction medium. The second reagent portion is released into the reaction medium and allowed to react. At an approximate time in the reaction the first reagent portion is released. The first reagent is then free to react with the second reagent and other components of the reaction medium.

Preferably, the releasing of the first reagent portion is by either raising the temperature of the reaction mixture to a temperature greater than or equal to the melting point of the carrier wax or by the addition of a solvent capable of dissolving the carrier wax.

The present invention is also a method of preparing a stabilized reagent preparation. This method comprises the steps of combining a substantially purified preparation of at least one biological or chemical reagent with a first carrier wax. Both the first carrier wax and the first reagent preparation are preferably in a liquid form. The combined reagent and carrier wax mixture is cooled at a sufficiently low temperature and for a sufficient time so that the combined mixture solidifies forming a first reagent portion. The first reagent portion is then exposed to an inactive form of a second reagent, which forms a second reagent portion.

The embodiments above describe a reagent preparation and delivery system in which two reagent portions are employed. The present invention is envisioned to encompass additional reagent preparations. For example, a third and fourth reagent portion may be exposed to the solidified first and second reagent portions. These additional reagents may also be sequentially released.

One object of the present invention is to provide a reagent preparation capable of room temperature storage in the presence of other reagents which would otherwise interact with one another.

Another object of the present invention is to deliver reagents in a chemical reaction in such a manner that the reagent is initially in an inactive form and is subsequently released in an active form.

Another object of the present invention is to provide a rapid method for creating stabilized reagents.

Another object of the present invention is to provide a method of sequentially delivering at least two reagent portions.

It is a feature of the present invention that the storage and delivery method is easily and inexpensively accomplished.

It is an advantage of the present invention that reagents may be stored at room temperature.

It is another advantage of the present invention that many different waxes may be used as carriers.

It is another advantage of the present invention that the second reagent portion may be stored in a second carrier wax, in a dehydrated matter, or in a glassified form.

Other aspects, objects and advantages of this invention will become apparent from a study of the specification and claims.

DETAILED DESCRIPTION OF THE INVENTION

1. In General

The present invention is a preparation and method for storing and delivering reagents in a manner that permits room temperature storage with a minimal amount of loss of reagent activity. By "reagent" we mean any substance that could be a component in a chemical or biochemical reaction, such as enzymes, peptide hormones, structural proteins, amino acids, antibodies, molecules containing protein groups (such as glycoproteins), RNA, DNA, nucleic acids, primers, buffers, and proteins conjugated to nucleic acids. A reagent could also be a detection substance. A detection substance could be useful to detect the presence of another reaction component, such as a protein or nucleic acid. A nucleic acid intercalating fluorophore, such as ethidium bromide, is a particularly advantageous embodiment.

By "substantially pure preparation of a reagent" we mean that the reagent preparation does not contain substantial amounts of a substance that would be detrimental to the ultimate reagent activity.

The present invention provides a reagent preparation that is capable of sequential delivery of separately stored reagents. By "sequential delivery" we mean that one reagent is delivered in an active form to a reaction mixture while the other reagent remains in an inactive form. In the present invention, the reagent preparation is designed to be exposed to a reaction medium. A second reagent portion is released and is free to interact with components of the reaction medium and with itself. At an approximate time in the reaction, a first reagent portion is released and is free to react with the second reagent portion and components of the reaction medium. The reaction medium may be a aqueous solution of buffers or other biological or chemical components or may simply be water.

For example, the reagent preparation of the present invention might be a wax-embedded enzyme covered with a dehydrated nucleic acid preparation. Water (the "reaction medium") is added to the preparation to release the nucleic acid. At an appropriate time, the preparation is heated above the melting temperature of the first carrier wax and the enzyme is released. The nucleic acid and the enzyme may then interact.

Preparation of wax-embedded reactions is described below. Dehydrated and freezed dried biological and chemical reagents are described in L. R. Rey, "Glimpses into the Fundamental Aspects of Freeze-drying," in *International Symposium on Freeze-drying of Biological Products, Washington, D.C.* 1976 in *Develop. Biol. Standard* 36:19–27, 1977 (S. Karger, Basel). This document is incorporated by reference as if fully set forth below.

Alternatively, the second reagent may be preserved in a "glass" made of polysaccharides. The formation of glasses is described in U.S. Pat. No. 5,250,429 (issued Oct. 5, 1993; inventors; Jolly, et al.) and U.S. Pat. No. 5,098,893 (issued Mar. 24, 1992; inventor: Franks), both of which are incorporated by reference. As before, water would be added to rehydrate the glassified DNA and at an appropriate time the first reagent would be released.

Other methods of stabilization of reagents are also approximate for the second reagent portion. It is necessary that the stabilization methods results in a inactive, stabilized preparation that is capable of being activated in a sequential matter. By "sequential matter" we mean that one portion of reagents is activated while another portion of reagents remains inactive.

To create a stabilized reagent, typically a liquified form of the reagent is first added to a liquified form of a carrier material. Alternatively, the purified reagent may be in solid form, such as when freeze-dried or dried by evaporative methods. For enzymes, either the liquified or dried form of the reagent may preferably be obtained from a purified enzyme preparation. In the examples below, we obtained liquified protein reagents from commercial enzyme preparations.

The carrier material for the first reagent is a wax and is described below. A liquified form of the carrier material may be prepared by heating the carrier wax material to its melting point. The liquified reagent and the liquified carrier material are mixed and immediately cooled to form a solid. We call this procedure "co-solidification".

The present invention is suitable for more than one protein reagent to be co-solidified. It could be advantageous in a biochemical or chemical reaction to add one aliquot containing several different reagents to a reaction.

Once the reagent has been co-solidified with the wax carrier material, the reagent is stable at room temperature storage for extended periods of time. For example, the Examples below disclose that the enzyme Bst E II can be stored at 37° C. for at least six weeks after co-solidification. αM13HRP conjugate can be stored for at least one week at 37° C. and Tth restriction enzyme can be stored at least six weeks at room temperature. Additionally, we show that protein reagents in combination with other PCR reagents are stable at least for six weeks at room temperature.

The second reagent is stored in an inactive form, but is not necessarily stored in a wax carrier. It is only necessary that the second reagent be stored in a manner that renders it incapable of reacting with the first reagent, capable of long-term storage (preferably at room temperature), and capable of being released. Examples of suitable storage for the second reagent are dehydration, glassification, and wax carrier.

The present invention is also a method of sequentially delivering reagents in a chemical or biochemical reaction. As described above, delivery of reagents in accordance with the present invention is by combining the reagent preparation and a reaction medium preferably an aqueous solution that contains other reagents meant to react to the reagent preparation. The second reagent portion is released and is free to react with materials in its environment. At an appropriate time, the co-solidified first reagent portion is then released from the carrier wax. Preferably, this release is obtained by subjecting the entire mixture to a temperature that exceeds the melting point of the carrier wax or by adding a solvent, such as xylene, which dissolves the carrier wax. The second and first reagents portions are now free to react.

After release of the reagent from the carrier wax, the carrier wax will form a separate layer on the reaction surface. This layer may be removed, preferably by xylene or with a pipette. Alternatively, this layer may remain in place to form a vapor barrier for the reaction mixture and prohibit evaporation of the reaction mixture.

One may remove the carrier wax with xylene or toluene, preferably by adding the solvent to the co-solidified mixture, incubating at 37° C. and vortexing the mixture. The solvent will dissolve the wax, which can then be extracted or evaporated.

A concentrated stock of the first reagent is preferably mixed with the carrier wax. In this manner, a small amount of the co-solidified product would need to be added to the reaction mixture to deliver a sufficient quantity of the reagent. Additionally, a concentrated protein reagent provides more stability for the protein. A concentrated solution of reagents might contain enzymes, buffer, salts and nucleotides. This solution is prepared using suitable methods known in the art of molecular biology. Generally, the co-solidified mixture is formulated such that the appropriate reaction concentrations of individual active materials will be delivered.

The co-solidified reagents are stored below the melting point of carrier material. Preferably, the materials are stored at room temperature.

2. Protein Reagents

Protein reagents that are suitable for the present invention include enzymes, peptides, structural proteins, amino acids, antibodies, protein conjugates with nucleic acids, and antibody conjugates. However, other protein reagents are suitable.

Protein reagents suitable for the present invention will lose minimal activity when added to a carrier wax at the melting temperature of the carrier wax. Enzymes are particularly advantageous choices as reagents. Some enzymes, such as the restriction enzyme Hind III, are capable of brief incubation at 60°–70° C., the melting point of a preferable wax carrier, although these reagents would be unstable at a prolonged exposure to this temperature. Preferable enzymes that may be stabilized and delivered by the present invention are restriction enzymes, DNA ligase, RNA polymerase, and reverse transcriptase.

The present invention is particularly useful for the delivery of thermostable enzymes. Preferred thermostable enzymes are DNA polymerase from thermophilic bacteria and restriction enzymes such as Bst E II, Taq I and Tth III. Reaction buffers can be added to the stabilized mixture and delivered by the present invention.

One method of determining whether a protein would be a suitable reagent for the present invention is to combine the protein with a carrier wax and determine the activity of the protein after a test storage period. A suitable test storage period would be room temperature storage for two weeks. If the preparation still exhibited requisite protein characteristics, such as enzyme activity if the protein is an enzyme or structural integrity if the preparation is a structural protein, then the protein is a suitable reagent. It is not necessary that the reconstituted protein preparation exhibit 100% of the examined characteristic. For instance, an enzyme may lose some activity in storage and still be a useful preparation. In general, an enzyme should not lose more than 50% enzyme activity in a two week room temperature storage and a structural protein should not degrade more than 50% in a two week room temperature storage. Note that in many types of protein stabilization methods, a large percentage of the ultimate loss takes place during the initial procedure.

3. Other Reagents

Another class of preferred reagents for the present invention are nucleic acid polymers, such as DNA and RNA, and individual nucleic acids, such as dideoxynucleotides, ribonucleotides and dideoxynucleotides. Preferentially, these nucleic acids would be combined with stabilizing buffers or other components.

Buffers and other chemical reaction components are also preferred reagents for the present invention. Detergents, cells and tissues are other reagents that may be used.

4. Carrier Waxes

By "carrier wax" we mean any of a group of substances composed of hydrocarbons, alcohols, fatty acids and esters that are solid at ambient temperature. These substances may be of plant or animal origin and contain principally esters of higher fatty acids and higher alcohols, free fatty acids and alcohols, and saturated hydrocarbons. A suitable carrier wax will be heat-sensitive such that the carrier will be liquid at a certain temperature and solid at a lower temperature. Additionally, a suitable wax will not be soluble or swellable in an aqueous solution. Preferably, the carrier wax is selected from material that has a melting point above room temperature. Most preferably, the carrier wax is selected from material that has a melting point above 37° C. so that at normal variations of room temperature the co-solidified material is always a solid.

Selection of a suitable carrier material is dependent upon the temperature stability of the reagent. The reagent must remain stable at the melting temperature of the carrier wax because both materials must be maintained, at least for a brief period of time (preferably 2–3 minutes), at the melting temperature of the carrier wax. Examples of waxes particularly suitable for the present invention are paraffin, AMPLIWAX PCR GEM 100 (Perkin Elmer Cetus) and POLYFIN (Poly-sciences). However, many other waxes are equally suitable.

One method of determining whether a candidate carrier wax is suitable for the present invention is to co-solidify the candidate wax with an enzyme or other protein known to be successfully stored in wax. The examples below disclose several restriction enzymes, DNA polymerases, and DNA ligase which would all be suitable test proteins. After co-solidification at a test period of time, for example, room temperature storage for two weeks, the co-solidified mixture is melted and the activity of the protein measured. If a requisite amount of protein activity is obtained after this test-storage period, then the candidate wax is suitable for the present invention. Control samples of the same enzyme or protein stored without wax can be stored alongside the co-solidified mixture to determine the activity differential due to storage in a carrier wax. If the ultimate goal is stabilization, a successful carrier wax will enable at least a two-fold difference in activity after a two-week room temperature storage period.

We envision that one could prepare suitable waxes by combinations of waxes. This may be to obtain a wax with a suitable melting point or to obtain a wax with other useful characteristics.

5. Creation of a Reagent Preparation

The present invention is a reagent preparation comprising at least a first and second reagent portion. The first reagent portion comprises at least one biological or chemical reagent and a first carrier wax. This first reagent portion may be in many physical forms. It may coat an inert solid support, such as a comb, dipstick or bead, or it may coat the bottom of a tube. The first reagent portion may coat a thin gold film, such as purchased from Pharmacia, Biosensor. (Coating on a thin gold film may be useful in an application that requires nanoliter levels of materials.) Other preferable materials for a solid support include glass, plastic, cellulose, both porous and nonporous materials, magnetic materials (such as iron), and metallic materials. The solid support may remain in a solidified form or liquify at an appropriate point in the reaction.

Alternatively, the first reagent portion may form a bead or wafer without other solid support.

The second reagent portion comprises at least one inactive biological or chemical reagent. This reagent portion is preferably dehydrated, glassified, or embedded in a second wax carrier. The second reagent portion may also take several forms. If the first reagent portion encases a solid support, such as a bead, comb, or dipstick, the second reagent portion may coat the first reagent portion. Alternatively, if the first reagent portion coats the bottom of a tube, the second reagent portion may form a layer on top of the first reagent portion. If the first reagent portion is a drop or wafer, the second reagent portion may coat the drop or wafer.

It is not necessary that the second reagent completely coat the first reagent. The second reagent need only be available to the reaction medium. For example, a reaction tube may contain a wax-embedded first reagent on one side of the tube and a dehydrated second reagent portion on the other side of the test tube.

If a third or fourth reagent portion is requested, these reagent portions are similar also present and available to the reaction medium. For example, if the first and second reagent portions are embedded in wax of different melting points and coated onto the bottom of a reaction vial, the third reagent portion may be a glassified preparation also present in the bottom of the reaction vial.

Figures 1, 2:
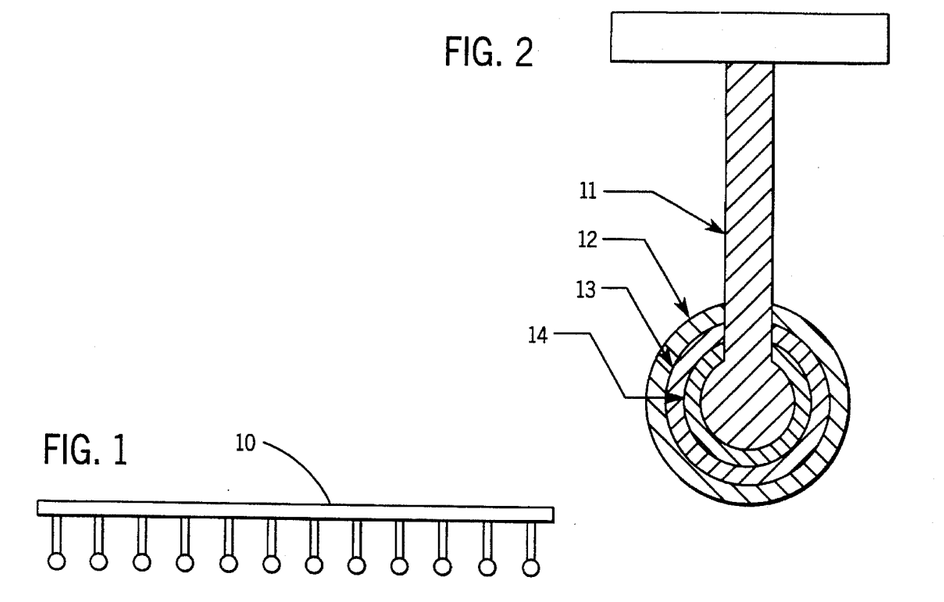
FIG. 1 is a side elevational view of a comb that forms a preferred embodiment of the present invention.
FIG. 2 is a cross-sectional view of the comb of FIG. 1.
Figure 3:
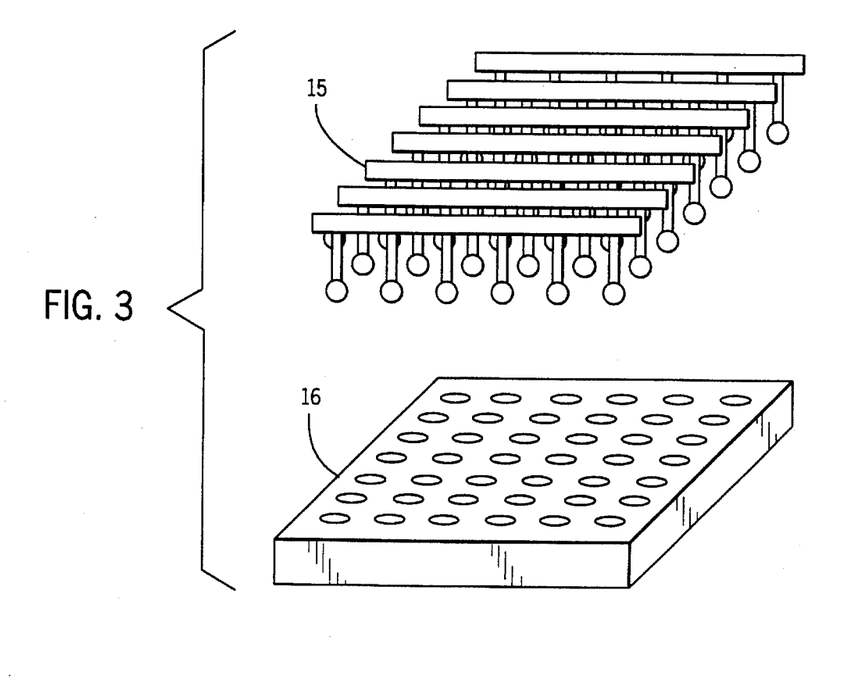
FIG. 3 is an exploded perspective view of a preferred use of the comb of FIG. 2.

One example of an advantageous form of the invention involves a comb designed to be placed in several reaction vessels. The teeth of the solid comb may be coated with streptavidin. The first reagent portion could be Taq polymerase and nucleic acid primers and encases the streptavidin. The second reagent portion is reverse transcriptase and dNTPs and is preserved in a glassified form. The second reagent portion encases the first reagent portion. One can use this preparation to perform cDNA synthesis, then amplify the cDNA, and then capture the amplified product by use of biotin/streptavidin binding. FIGS. 1–3 are diagrams of the embodiment described above.

FIG. 1 discloses a comb 10. FIG. 2 is a cross-section of one of the teeth of the comb 10 and shows solid substrate 11; sugar plus reverse transcriptase plus dNTPs 12; wax plus taq polymerase plus primers 13; and streptavidin 14. FIG. 3 shows the relationship between the capture combs 15 and capture plate 16.

This particular embodiment of the present invention may be useful in a situation where one would grow cells in a cell culture plate, which would form the reaction vessel described above. The wells of the cell culture plate could be coated with trypsin embedded in wax also containing lysis reagents such as buffer and lysozyme. After growing the cells at 37° C., one could raise the temperature to 55° C., melt the wax, release the reagents, and permit cell lysis. One would then insert the comb, which comprise sequential reagents sufficient to capture/amplify the DNA/RNA.

Another example of an advantageous form of the present invention involves a cellulose bead/membrane with an attachment moiety such as anionic or cationic molettes, antibodies or enzymes such as streptavidin or RNAse H. This bead could be encased by wax-embedded buffers, NTPs and enzyme. One would add a nucleic acid template or primer as a second reagent coating. After dissolving the second reagent coating, one could raise the temperature, melt the wax-embedded reagents and perform an amplification step. The cellulose bead would be suitable to capture the product molecules.

EXAMPLES

In the examples below, we have specifically demonstrated that the present invention is suitable for enzymes useful in PCR reactions, thermophilic restriction enzymes, DNA sequencing enzymes, conjugated antibodies, lysozyme, and DNA ligase. These examples are meant to be specific embodiments of the present invention and are not meant to imply that other protein reagents are not equally suitable for the present invention.

To demonstrate the sequential delivery of wax embedded reagents, we have disclosed a simple system consisting of first strand cDNA synthesis followed by PCR amplification of the cDNA. The first reagent portion comprises wax embedded reagents necessary for PCR amplification. The second reagent portion comprises dehydrated reagents necessary for first cDNA synthesis.

Example 1

Polymerase Chain Reaction (PCR)

In general, PCR enables one to amplify specific segments of nucleic acid by annealing specific primers to the nucleic acid that one wishes to amplify and allowing a polymerase enzyme to polymerize the nucleic acid between the two primers. The reaction product is heated to dislodge the primers from their specific targets. When the synthesized nucleic acid anneals with other primers in the reaction mixture, an exponentially increasing amount of nucleic acid is formed.

We demonstrated that different combinations of protein reagents and other reagents involved in PCR could be stored and delivered by the present invention. In Example 1(A) the polymerase is co-solidified with buffers and nucleotides. In Example 1(B), the primers, the nucleotides, the enzyme and the PCR buffers are stored. Of course, many different combinations of protein with other components are possible.

In the following reactions, when AmpliWax was used for co-solidification, a standard method was used to add the liquified reagent to the carrier wax. One pellet of the AmpliWax was melted at 65° C. for two to three minutes. The liquified reagent was added to the side of the tube and the mixture remelted at 65° C. The mixture was then vortexed gently. The reaction was cooled at 22° C. for two minutes. After cooling, the reaction was in a solid form.

To mix the reactants in Example 1(A), water, primers and DNA were placed on top of the co-solidified reagents. The mixture was melted, vortexed and cooled. After cooling, the wax layer formed a solid shell at the top of the reaction mixture. The wax layer was not disturbed and the PCR reaction was subjected to the standard reaction conditions. In Example 1(B), the wax was melted, vortexed and cooled. The reagents were moved as a layer from beneath the wax.

As a test of storage stability, the co-solidified reagents were stored at various temperatures for various periods of time. The reagents in Examples 1(A) and 1(B) were stored for up to six weeks at ambient temperature.

A. Storage of DNA Polymerase

Taq DNA Polymerase (0.5 μl, 2.5 units; Perkin Elmer or Pharmacia) was added to one liquified AmpliWax PCR Gem (Perkin Elmer) with 2 μl of 50x PCR Buffer (0.5M Tris-HCl, pH 8.3, 2.5M KCl, 0.075M MgCl$_2$) and 1 ul of 100x Polymerization Mix (20 mM each of dGTP, dATP, dTTP, dCTP; Pharmacia). The co-solidified material was stored for up to six weeks. One sample was stored at 37° C. for four weeks.

PCR amplification was performed by adding 100 ul of water containing 1 ng of pBR322 DNA linearized with PvuII and complementary primers specific for the pBR322 sequence (50 pmoles each of SF4 and SF5 primers, Pharmacia) to the co-solidified mixture. The reaction mix was placed in a Perkin-Elmer Cetus thermocycler (Perkin-Elmer Cetus, Norwalk, Conn.) under the following temperature cycling protocol: 30 cycles, each cycle consisting of denaturation at 94° C. for 1 minute, annealing at 55° C. for 2 minutes, and extension at 72° C. for 2 minutes. As a control, an identical PCR reaction was performed with reagents that had not been co-solidified or stored at elevated temperatures.

To verify the efficacy of the PCR reaction, 10 ul of the completed PCR reaction was analyzed by agarose gel electrophoresis in 1x TBE buffer containing ethidium bromide. An amplification product of approximately 350 bp of approximately the same yield was observed with both fresh reagents (control) and wax-embedded reagents stored at 37° C. for four weeks. Results were similar with all the stored samples.

B. Heat-Soaked PCR 50 pmoles each of SF4 and SF5, 0.2 mM each of dNTPs (Pharmacia), 2.5 units AmpliTaq and PCR Buffer (Perkin Elmer) were co-solidified and stored. The co-solidified mixture was melted, as described above, and the reagents removed from beneath the wax layer. 90 ul of water containing 1 ng of pBR322 DNA cut with PvuII was heat denatured at 94° C. for 30 minutes and added to the reagents.

PCR reaction was performed as above. The results with co-solidified reagents were comparable to control reactions with standard Heat-Soaked reagents and technique (Ruanoet, et al., *BioTechniques* 13(2):266–274 (1992)). We obtained nucleic acid of equivalent amounts and size. Therefore, the protein reagent was successfully stored and delivered by the manner of the present invention.

Example 2

Thermophilic Restriction Enzymes

Thermophilic restriction enzymes (one unit) were co-solidified with AmpliWax as described in Example 1.

A. DNA Restriction Analyses: Bst EII

One unit of Bst EII was co-solidified with carrier wax and stored at 37° C. for six weeks. Hydrolysis of lambda DNA (0.5 μg) was performed at 60° C. for 1 hr with both fresh (control) and the co-solidified enzyme. Lambda DNA in buffer was added on top of the co-solidified mixture. The entire mix was melted at 65° C., vortexed, and incubated at 60° C. for digestion.

Complete hydrolysis of lambda DNA was observed with wax-embedded Bst EII. However, Bst EII stored at 37° C. without carrier wax was completely inactive after ten days.

B. DNA Restriction Analyses: Taq I

One unit of Taq I was co-solidified with carrier wax as above for six weeks at room temperature. Hydrolysis of lambda DNA (0.5 μg) was performed at 65° C. for 1 hr with both fresh and co-solidified enzymes. Complete hydrolysis of lambda DNA was observed with the co-solidified Taq I.

C. DNA Restriction Analyses: Tth 111 I

One unit of Tth 111 I was co-solidified with carrier wax as above. Hydrolysis of lambda DNA (0.5 μg) was performed at 65° C. for 1 hr with fresh and wax-embedded enzyme that had been stored at room temperature for six weeks. Complete hydrolysis of lambda DNA was observed with co-solidified Tth 111 I.

Example 3

DNA Sequencing With Tth/Bst DNA Polymerases

Control sequencing reactions were performed according to procedures recommended by the manufacturers (GeneAtaq Kit; Pharmacia and BioRad for the Bst reaction).

Two units of Bst or one unit of Tth were co-solidified with wax as in Example 1 and stored for one week at room temperature for Bst or two weeks at room temperature for Tth. The sequencing reaction was as follows:

Annealed template and primers and P-α-dATP were added to the co-solidified sample. The mix was heated until melting, vortexed and cooled. The solution was removed from beneath the wax for the subsequent reaction.

Sequencing results with co-solidified enzymes were comparable to control reactions. We observed equivalent extension and lack of background.

Example 4

HRP-Conjugated α-M13 antibody

α-M13 HRP conjugate, a sheep antibody to M13 conjugated to horseradish peroxidase (HRP), was co-solidified with carrier wax as described in Example 1. The co-solidified product was stored for one week at 22° C. or 37° C. HRP was conjugated to αM13 antibodies using the periodate coupling method (*Antibodies, A Laboratory Manual*; Ed:Harlow and Lane, 1988).

To demonstrate binding, microtiter plate wells were coated with M13KO7 phage supernatant. The αM13HRP conjugate was bound by standard methods. The wells were washed and a colorimetric substrate was added. The color change, indicative of the amount of functional conjugates bound to the M13K07 coated on the well, was measured.

After one week at 22° C. or 37° C., co-solidified α-M13 HRP conjugate showed good signal on ELISA while α-M13 HRP conjugate that had not been co-solidified showed background levels, thus demonstrating that the wax can stabilize the α-M13 HRP conjugate. Co-solidified antibody that had been stored for one week at 22° C. or 37° C. showed approximately half of the signal obtained with a control conjugate that had been stored at 4° C. without co-solidification.

Example 5

DNA Ligation

Ampligase, a thermostable T4 DNA ligase (1 Unit, Epicenter, Madison) was co-solidified with melted AmpliWax and stored for one day at 37° C. Ligation of Sma I-/Sal I-cut lambda DNA with fresh and wax-embedded ligase showed successful results. DNA, buffer and water were added to the top of the co-solidified preparation. The entire mixture was melted by incubating at 65° C. for 10 minutes, vortexed and cooled. The ligation reaction was at 70° C. for 10 minutes. Ligation products were compared to controls by pattern of bands after electrophoresis.

Example 6

Hind III

One unit of Hind III (Pharmacia) was co-solidified with AmpliWax, as described above. A mixture of 1 µg lambda DNA, reaction buffer and water was added to the co-solidified enzyme. The tube was heated at 65° C. until melted (about two minutes), vortexed and cooled to room temperature. Digestion was performed at 37° C. for one hour. Results indicated that the lambda DNA had been digested. The Lambda DNA appeared to be completely digested, as did the DNA sample incubated with the non-co-solidified Hind III.

Example 7

Klenow Fragment

5–10 units of Klenow DNA polymerase (Pharmacia) were co-solidified, as above, with AmpliWax. The preparation was not stored and was used immediately. Annealed template and primer was added to the co-solidified mixture. The mixture was heated at 65° C. for about two minutes, vortexed, and cooled to room temperature. The liquified reagents were removed from beneath the wax layer and transferred to a new tube. DNA sequencing reactions were performed with BaseMaster Sequencing Kit according to instructions. Results were comparable to those using fresh enzyme. We observed equivalent extensions and low backgrounds.

Example 8

Paraffin Wax

Reagents for PCR amplification (buffer, nucleotides and Taq DNA Polymerase) were co-solidified as above in Paraffin Wax and successfully stored and delivered. 10 ul of 10X PCR Buffer, 1 ul of 20 mM dNTPs and 1 ul of Taq DNA Polymerase (Pharmacia) were co-solidified in approximately 20 mg Paraffin Wax from Aldrich Chemical Company, Inc. (Product number 32,720-4). The Paraffin Wax melted at about 65° C. Water, primers (50 pmoles each) and DNA template (1 ng) were added to the co-solidified reagents. The tube was heated to 65° C., vortexed and cooled to room temperature. PCR amplification was performed as follows: 94° C., 1 min.; 55° C., 2 min.; 72° C., 2 min., 30 cycles. Successful results were obtained, comparable to those using fresh reagents. We observed molecules of equivalent size and amounts.

Example 9

Xylene and Toluene Extraction

PCR Buffer, nucleotides and Taq DNA Polymerase were co-solidified in Ampliwax, as above. 100 ul of xylene or toluene was added on top of the co-solidified reagents. The tube was incubated for 30 minutes at 37° C. with vigorous vortexing about every five minutes. The dissolved wax and solvent were removed by pipetting. Water, primers and DNA template were added to the remaining agents. An Ampliwax pellet was added on top to prevent evaporation. The standard cycle program was used. A PCR product of the expected size was generated.

Example 10

Sequential Delivery

In General

The following example illustrates sequential delivery of reagents by the method of the present invention. Reagents necessary to perform PCR are co-solidified with a wax carrier to form a first reagent portion. A dried (or dehydrated) mix capable of making a cDNA preparation from an RNA template forms a second reagent portion and is coated onto the first reagent portion.

The example below contains control reactions in which the cDNA reaction mixtures are not dehydrated. The example demonstrates that the sequential delivery of the present invention works as well as when "wet" or non-dehydrated cDNA mixes are used. The sequential delivery preparation of the present invention has the advantage of room temperature storage and inactivation of the second reagents.

Materials & Methods

First reagent portions (PCR reaction mix cosolidified in a wax carrier) were made by mixing 1 µl each of PCR primers (≈37 pmol each), 1 µl (5 units) of AMPLITAQ (Perkin Elmer), 5 µl 60% sucrose, and 0.1% cresol red in 1 melted AMPLIWAX PCR GEM 100 held at 65° C. for each reaction. To avoid phase separation of the wax and liquid components the material was vortex-mixed while cooling.

A cDNA first strand synthesis mix comprises the second reagent portion. This mix is added to the surface of the solidified first reagent portion. In one set of reactions, the first strand mix is kept in solution. In a second set of reactions, the first strand mix is dehydrated.

The final concentration of the cDNA first strand mix is 50 mM Tris-HCl, pH 8.6, 75 mM KCl, 10 mM $MgCl_2$, 7.5 mM dithiothreitol, 75 µg/ml bovine serum albumin (DNAse free), 30 units RNAguard® (Pharmacia Biotech, Milwaukee, Wis.), and 120 units MMLV reverse transcriptase, 0.2 µg pd($N_6$) primer in a reaction volume of 33 µl. For the dehydrated cDNA reactions, the aqueous cDNA reagent mixture was pipetted on top of the solidified first reagent portion in the bottom of a 0.5 ml DEPC treated polypropylene tube. Drying was performed at 10° C. for 16 hr at a vacuum of about 50 mtorr followed by an additional drying at 20° C. for 4 hr at about 50 mtorr.

For the first strand cDNA reactions essentially the following protocol was used with 1 ng of rabbit globin mRNA (BRL) for each 33 µl reaction (37° C., 1 hr).

After the completion of the cDNA reaction, we began PCR amplification. For the PCR reactions, the complete cDNA reaction was diluted to 97 µl with MilliQ® water. About 37 pmol each of rabbit globin upstream and downstream primers were used (Pharmacia IM #'s 32014 and 32012 respectively) along with 5 units of Amplitaq DNA polymerase. No sucrose was present in the "liquid PCR" reaction lanes. The samples were cycled 30 times. Denaturation was at 95° C. for 1 minute followed by a 30 seconds 60° C. annealing and a 72° C., 30 seconds extension in each cycle.

The samples were analyzed on a 1.5% agarose gel in a GNA 100 apparatus (5 µl/well) in Tris-Acetate buffer containing 0.25% ethidium bromide. An amplified band of the correct size was seen in all samples. Analysis of reaction in which the cDNA was dried onto the PCR/wax mix indicated that the sequential delivery of reagents was successful.

We claim:

1. A reagent preparation comprising:
   (a) a first reagent portion comprising:
   (i) an amount of a wax carrier, the wax carrier having a first melting point, and
   (ii) an amount of a first reagent wherein said first reagent is a preparation of at least one biological or chemical reagent, said first wax carrier and said first reagent being combined to form a solid first reagent portion when stored at a temperature less than the first melting point, and
   (b) a second reagent portion comprising at least one chemical or biological reagent stored in an inactive form, wherein the first and second reagent portions are capable of sequential delivery into a chemical reaction and wherein the second reagent portion is at least partially coated, covered or layered upon the first reagent portion.

2. The preparation of claim 1 wherein the first melting point is greater than approximately room temperature.

3. The preparation of claim 1 wherein the first melting point is greater than approximately 37° C.

4. The preparation of claim 1 wherein the first melting point is greater than approximately 60° C.

5. The preparation of claim 1 wherein the second reagent portion is stored in a glassified form.

6. The preparation of claim 1 wherein the second reagent portion is stored in a second carrier wax.

7. The preparation of claim 1 wherein the second reagent portion is stored in a dehydrated form.

8. The preparation of claim 1 wherein either the first or second reagent portion comprises an enzyme selected from the group consisting of DNA polymerases, RNA polymerases, nucleic acid modifying enzymes, ligases, lysozymes, RNAses, DNAses, and restriction enzymes.

9. The preparation of claim 1 wherein either the first or second reagent portion additionally comprises a buffer.

10. The preparation of claim 1 wherein either the first or second reagent portion comprises a plurality of reagents.

11. The preparation of claim 1 wherein either the first or second reagent portion comprises proteins and nucleic acid polymers.

12. The preparation of claim 1 wherein the first carrier wax contains paraffin.

13. A method of delivering a biological or chemical reagent in a chemical reaction comprising the steps of:
   (a) obtaining the preparation of claim 1 and exposing it to a reaction medium,
   (b) releasing the second reagent, wherein the second reagent portion is free to interact with components of the reaction medium, and
   (c) then releasing the first reagent portion, wherein the first reagent portion is free to react with the second reagent portion and components of the reaction medium.

14. The method of claim 13 wherein the releasing of the first reagent portion is by raising the temperature of the reaction mixture to a temperature greater than or equal to the melting point of the carrier wax.

15. The method of claim 13 wherein the releasing of the first reagent portion is by the addition of a solvent capable of dissolving the carrier wax.

16. The method of claim 13 wherein the second reagent portion is stored in a glass form and the releasing of the second reagent is by the addition of an aqueous medium.

17. The method of claim 13 wherein the second reagent portion is stored in a second carrier wax and the releasing of the second reagent is by raising the temperature of the reaction mixture to a temperature greater than or equal to the melting point of the second carrier wax.

18. The preparation of claim 1 wherein the preparation additionally comprises an inert solid support.

19. The preparation of claim 18 wherein the solid support is selected from the group consisting of cellulosic materials, glass materials, magnetic particles, polystyrene, polypropylene, and metallic materials.

20. The preparation of claim 19 wherein the material is gold film.

21. The preparation of claim 1 wherein either the first or second reagent comprises a fluorophore.

22. The preparation of claim 21 wherein the fluorophore is a nucleic acid intercalating agent.

23. The preparation of claim 22 wherein the agent is ethidium bromide.

24. A method of preparing a stabilized reagent comprising the steps of:
   (a) combining a preparation of a first reagent with a carrier wax, wherein both the reagent preparation and the carrier wax are in liquid form;

(b) cooling the combined first reagent and carrier wax mixture at a sufficiently low temperature and for a sufficient time so that the combined mixture solidifies, wherein a first reagent portion is formed; and (c) combining the solidified first reagent portion with a second reagent portion comprised of at least one biological or chemical reagent stored in an inactive form, wherein the second reagent portion is at least partially coated, covered or layered upon the first reagent portion.

25. The method of claim 24 additionally comprising the step of solidifying the combined mixture of step (b) on a solid support.

26. The method of claim 24 wherein the second reagent has been air-dried or freeze-dried.

* * * * *